United States Patent [19]
Siddall et al.

[11] Patent Number: 6,015,911
[45] Date of Patent: Jan. 18, 2000

[54] PROCESS FOR PREPARING 1-ALKYL-4-(2-CHLORO-3-ALKOXY-4-ALKYLSULFONYLBENZOYL)-5-HYDROXYPYRAZOLE AND RELATED COMPOUNDS

[75] Inventors: Thomas L. Siddall, Zionsville, Ind.; Mark V. M. Emonds, Midland, Mich.; Karl L. Krumel, Midland, Mich.; Jennifer M. Schomaker, Midland, Mich.; Mark W. Zettler, Carmel, Ind.

[73] Assignee: Dow AgroSciences LLC, Indianapolis, Ind.

[21] Appl. No.: 09/047,173

[22] Filed: Mar. 24, 1998

Related U.S. Application Data

[60] Provisional application No. 60/042,349, Mar. 24, 1997.

[51] Int. Cl.[7] .................... C07D 231/20; C07D 231/08; C07D 403/12; C07C 315/00; C07C 323/00; C07C 319/00
[52] U.S. Cl. .................... 548/369.4; 548/364.1; 548/365.7; 548/366.1; 548/366.4; 548/366.7; 548/367.1; 562/429; 562/432; 562/474; 562/840; 568/35
[58] Field of Search ............... 548/366.4, 366.1, 548/365.7, 366.7, 367.1, 364.1, 369.4; 568/35; 562/429, 432, 474, 840

[56] References Cited

U.S. PATENT DOCUMENTS

| | | | |
|---|---|---|---|
| Re. 34,408 | 10/1993 | Tanaka .................. | 548/369.4 |
| Re. 34,779 | 11/1994 | Oya et al. ............... | 504/282 |
| 4,744,815 | 5/1988 | Baba et al. .............. | 548/367 X |
| 4,885,022 | 12/1989 | Baba et al. .............. | 548/367 X |
| 4,898,973 | 2/1990 | Lee ....................... | 562/429 |
| 5,001,256 | 3/1991 | Michaely et al. ......... | 560/65 |

FOREIGN PATENT DOCUMENTS 63-122673  5/1988  Japan .

OTHER PUBLICATIONS

V. V. Grushin et al., J. Chem. Soc., 1992, 611–612.
M. Huser et al., Angew. Chem. Int Ed. Engl., 28, 1386–1388 (1989).
Y. Ben–David et al., J. Am. Chem. Soc., 111, 8742–8744 (1989).
V. Dufaud et al,, J. Chem. Soc., Chem. Comm., 1990, 426–427.

*Primary Examiner*—Floyd D. Higel
*Attorney, Agent, or Firm*—D. Wendell Osborne; Craig E. Mixan

[57] ABSTRACT

Herbicidal 1-alkyl-4-(2-chloro-3-alkoxy-4-alkylsulfonylbenzoyl)-5-hydroxypyrazole compounds, as well as 1-halo-2-chloro-3-alkoxy-4-alkylsulfonylbenzene compounds and 2-chloro-3-alkoxy-4-alkylsulfonylbenzoic acid compounds, were prepared in good yield by the reaction of the corresponding 3-chloro compound with an alkali metal alkoxide compound. 1-Halo-2-chloro-3-alkoxy-4-alkylsulfonylbenzene and 1-halo-2,3-dichloro-4-alkylsulfonylbenzene compounds were converted to compounds having hydroxycarbonyl, alkoxycarbonyl, or 1-alkyl-5-hydroxypyrazole-4-carbonyl substituents in place of the 1-halo substituent by reaction with carbon monoxide and water, an alcohol, or a 1-alkyl-5-hydroxypyrazole compound, respectively, in the presence of a palladium II salt:trihydrocarbylphosphine complex type catalyst.

20 Claims, No Drawings

PROCESS FOR PREPARING 1-ALKYL-4-(2-CHLORO-3-ALKOXY-4-ALKYLSULFONYLBENZOYL)-5-HYDROXYPYRAZOLE AND RELATED COMPOUNDS

CROSS-REFERENCE TO RELATED APPLICATIONS

This application claims the benefit of U.S. Provisional Application No. 60/042349, filed Mar. 24, 1997.

BACKGROUND OF THE INVENTION

The present invention relates to a process for the preparation of herbicidal 1-alkyl-4-(2-chloro-3-alkoxy-4-alkylsulfonylbenzoyl)-5-hydroxypyrazole compounds and of certain 1-halo-2-chloro-3-alkoxy-4-alkylsulfonylbenzene compounds that are useful intermediates in the manufacture of these herbicidal compounds.

A number of 1-alkyl-4-(2-chloro-3-alkoxy-4-alkylsulfonylbenzoyl)-5-hydroxypyrazole compounds were disclosed in U.S. Pat. No. RE-34,779 and were reported to possess excellent herbicidal properties. These compounds were prepared by the reaction of a 1-alkyl-5-hydroxypyrazole compound with a 2-chloro-3-alkoxy-4-alkylsulfonylbenzoic acid compound. The preparation of the 2-chloro-3-alkoxy-4-alkylsulfonylbenzoic acid compounds used as starting materials was carried out by alkylation of 2-chloro-3-hydroxy-4-alkylsulfonylbenzoic acid compounds. The 2-chloro-3-hydroxy-4-alkylsulfonylbenzoic acid compounds required for this procedure can be obtained by hydrolysis of a 2,3-dichloro-4-alkylsulfonylbenzoic acid compound. This reaction and the alkylation process were disclosed in U.S. Pat. No. 4,898,973. The preparation of 1-alkyl-4-(2-chloro-3-alkoxy-4-alkylsulfonylbenzoyl)-5-hydroxypyrazole compounds by this route requires many reaction steps and produces large quantities of unusable by-products and waste. More direct and economical methods of production are highly desirable.

SUMMARY OF THE INVENTION

It has now been found that 1-alkyl-4-(2-chloro-3-alkoxy-4-alkylsulfonylbenzoyl)-5-hydroxypyrazole compounds can be prepared by the reaction of 1-alkyl-4-(2,3-dichloro-4-alkylsulfonylbenzoyl)-5-hydroxypyrazole compounds with alkali metal alkoxide compounds. The reaction takes place in a surprisingly selective manner and in a surprisingly high yield. It has also been found that certain 1-halo-2-chloro-3-alkoxy-4-alkylsulfonylbenzene compounds, which can be used as intermediates in the production of the same herbicidal compounds, can be prepared in the same way from 1-halo-2,3-dichloro-4-alkylsulfonylbenzene compounds in the same surprisingly selective manner and surprisingly high yield.

The primary process of the invention includes the preparation of 3-alkoxybenzene compounds of Formula I:

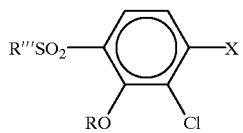

wherein
X represents Cl, Br, $CO_2H$, or a 1-alkyl-5-hydroxypyrazole-4-carbonyl moiety of Formula II:

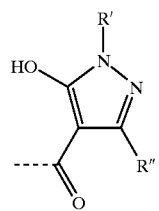

R represents a $C_1$–$C_4$ alkyl group optionally substituted with a $C_1$–$C_4$ alkoxy or $C_1$–$C_4$ alkylthio group or with a 3–6 membered alicyclic moiety composed of one oxygen or sulfur atom and 2–5 carbon atoms or represents a 3–6 membered alicyclic moiety composed of one oxygen or sulfur atom and 2–5 carbon atoms;

R" represents H or $C_1$–$C_4$ alkyl; and

R' and R'" each independently represents $C_1$–$C_4$ alkyl; which process comprises combining a 3-chlorobenzene compound of Formula III:

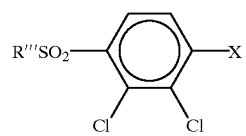

wherein X and R'" are as defined hereinabove
with an alkali metal alkoxide compound of Formula IV:

wherein
R is as defined hereinabove and
$M^+$ represents lithium, sodium, or potassium cation in a liquid medium, optionally in the presence of a phase transfer catalyst, at a temperature of about 20° C. to about 110° C.

A compound of Formula I wherein X represents a 1-alkyl-5-hydroxypyrazole-4-carbonyl moiety of Formula II is often preferably employed as the 3-chlorobenzene compound starting material. Sodium and potassium salts of 2-methoxyethanol are often preferred alkali metal alkoxide compounds of Formula IV. The process is most often used to prepare the compound 4-(2-chloro-3-(2-methoxyethoxy)-4-methylsulfonylbenzoyl)-1-ethyl-5-hydroxypyrazole or intermediates conveniently convertible to it.

Compounds of Formulas I and III wherein X represents chloro or bromo, which are valuable intermediates in the production of herbicides, are other embodiments of the invention.

The invention further includes processes for converting compounds of Formulas I and III wherein X represents chloro into compounds of Formulas I and III wherein X represents hydroxycarbonyl, alkoxycarbonyl, or a 1-alkyl-5-hydroxypyrazole-4-carbonyl moiety of Formula II, which processes involve their reactions with carbon monoxide in the presence of a palladium II salt:trihydrocarbylphosphine complex catalyst, such as the complex between palladium acetate and 1,4-bis(diphenylphosphino)butane.

DETAILED DESCRIPTION OF THE INVENTION

The primary process of the present invention can be characterized as a method of converting the chloro substituent in the 3-position of a 2,3-dichloro-4-alkylsulfonylbenzene compound of Formula III:

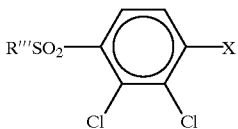

wherein X represents a chloro, bromo, CO$_2$H, or a 1-alkyl-5-hydroxypyrazole-4-carbonyl moiety of Formula II:

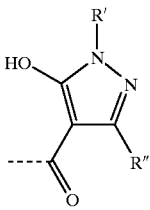

into an alkoxy substituent by selective nucleophilic substitution with an alkoxide ion reagent. The 3-position chloro substituent (chloro substituent ortho to the alkylsulfonyl substituent) reacts preferentially to the 2-position chloro substituent (chloro substituent meta to the alkylsulfonyl substituent) and, when present, the 1-position chloro or bromo substituent (chloro or bromo substitutent para to the alkylsulfonyl substituent). The products obtained are herbicidal 1-alkyl-4-(2-chloro-3-alkoxy-4-alkylsulfonylbenzoyl)-5-hydroxypyrazole compounds of Formula IA:

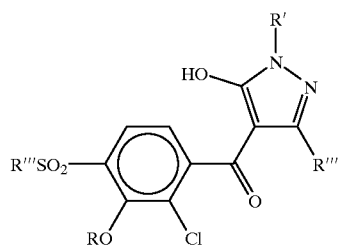

or compounds of Formula IB:

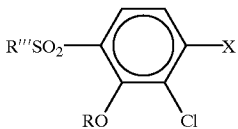

wherein X represents chloro, bromo, or CO$_2$H, and R, R', R", and R'" are as defined for compounds of Formula I in the Summary of the Invention. The compounds of Formula IB are useful as intermediates in the preparation of inter alia the herbicidal compounds of Formula IA.

The process of the invention is generally carried out by combining a 3-chlorobenzene compound of Formula III:

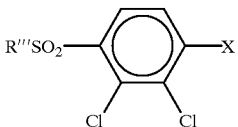

wherein R'" and X are as defined in the Summary of the Invention with an alkali metal alkoxide compound of Formula IV:

wherein R and M$^+$ are as defined in the Summary of the Invention under suitable reaction conditions.

The term 'alkyl' as employed herein includes normal, branched chain, and cyclic alkyl moieties. The alicyclic moiety substituents (R) of the invention are bonded through a carbon atom and are viewed as substituted cyclic alkyl groups.

R in Formulas I, IA, IB, and IV represents an alkyl group such a C$_1$–C$_4$ alkyl group optionally substituted with a C$_1$–C$_4$ alkoxy or C$_1$–C$_4$ alkylthio group or with a 3–6 membered alicyclic moiety composed of one oxygen or sulfur atom and 2–5 carbon atoms or represents a 3–6 membered alicyclic moiety composed of one oxygen or sulfur atom and 2–5 carbon atoms. Groups that are suitable R groups include methyl, ethyl, 1-methylethyl, butyl, cyclopropyl, 2-methoxyethyl, 3-ethoxypropyl, 2-methylthio-1,1-dimethylethyl, 3-(oxacyclopentyl)methyl, 4-oxacyclohexyl, and the like. C$_1$–C$_4$ alkyl groups and 2-(C$_1$–C$_4$ alkoxy)ethyl groups are often preferred. 2-Methoxyethoxy is usually an especially preferred group.

R' in Formulas I, IA, II, and III represents an alkyl group, including a C$_1$–C$_4$ alkyl group. Such groups include methyl, ethyl, 1-methylethyl, 1,1-dimethylethyl, and cyclo-propyl. Methyl and ethyl are generally preferred.

R" in Formulas I, IA, II, and III represents hydrogen or an alkyl group, including a C$_1$–C$_4$ alkyl group. Such alkyl groups include methyl, ethyl, 1-methylethyl, 1,1-dimethylethyl, and cyclo-propyl. Hydrogen is generally preferred.

R'" in Formulas I, IA, IB, and III represents an alkyl group including a C$_1$–C$_4$ alkyl group. Such alkyl groups include methyl, ethyl, propyl, 1-methylethyl, 1,1-dimethylethyl, and cyclo-propyl. Methyl is generally preferred.

X in Formulas I and III represents a halogen, including chloro or bromo, hydroxycarbonyl, or a pyrazole moiety, including a moiety of Formula II wherein R' and R" are as defined in the Summary of the Invention. A moiety of Formula II is generally preferred. The moiety of Formula II wherein R' represents methyl or ethyl and R" represents hydrogen is generally more preferred.

When X in Formula III represents chloro or bromo, the selective reaction of the 3-position chloro substituent with alkoxide ion to obtain a compound of Formula IB also takes place when the 2-position chloro substituent is replaced by a methyl, ethyl, bromo, methoxy, or ethoxy substituent. This is a further embodiment of the invention.

M$^+$ in Formula IV represents an alkali metal cation, including lithium, sodium, and potassium. Sodium and potassium cations are generally preferred. In some situations, it is also possible to use compounds of Formula IV wherein M$^+$ represents a magnesium or calcium cation.

Phase transfer catalysts generally accelerate the reaction and are often advantageously employed. Suitable phase transfer catalysts include crown ethers, for example, 18-crown-6, 12-crown-4, and benzo-15-crown-5; tetraalkylammonium salts, such as tetrabutylammonium bromide, methyltrioctylammonium chloride, and benzyltriethylammonium chloride; and tetraarylphosphonium salts, such as tetraphenylphosphonium bromide. 18-Crown-6 crown ether is sometimes preferred. About 5 to 20 mole percent of the catalyst is typically used.

The chemical reaction of the present invention can be effected by contacting the alkali metal alkoxide compound of Formula IV with the 3-chlorobenzene compound of Formula III under suitable reaction conditions. Suitable reaction conditions include temperatures of about 20° C. to about 110° C., preferably about 40° C. to about 90° C. It is sometimes advantageous to initiate the reaction at a lower temperature and to increase the temperature as the reaction proceeds. At higher temperatures the desired selectivity is lost and at lower temperatures the reaction is too slow. The reaction is typically carried out at atmospheric pressure, but pressure has little influence. The reaction mixture is typically agitated to ensure good mixing. The reaction is typically complete in about 0.5 to about 24 hours.

A solvent or mixture of solvents is generally employed to create a liquid reaction medium. Solvents that have been found to be useful are those in which the alkali metal alkoxide compound used has at least some solubility and which are not appreciably reactive with the starting materials or products under the reaction conditions employed. Such solvents include, for example, the alcohol (R-OH) from which the alkali metal alkoxide reagent of Formula IV is derived (ethanol, 2-methoxyethanol, 2-ethylthio-1-methylethanol, and the like), t-butyl alcohol, dioxane, tetrahydrofuran, 1,2-dimethoxyethane, and tetraethyleneglycol dimethyl ether. Dipolar, aprotic solvents, such as N-methyl-2-pyrrolidinone and N,N-dimethylformamide can be also be used, but the results are usually not as good due to by-product formation. The reaction mixture typically contains at least some of the alcohol from which the alkali metal alkoxide reagent was prepared and the use of said alcohol as the only solvent is often preferred.

Dry reagents are often employed and measures are often taken to exclude moisture from the system. Advantageous results are usually obtained when the water in the medium is kept below about 1.5 percent and are usually more pronounced when it is kept below about 500 ppm. This is a preferred embodiment of the invention, but is not a requirement.

The compound of Formula I produced can be recovered by conventional means or can be used without recovery from the reaction medium. When the solvent used is water soluble, it is often convenient to acidify the mixture with an acid such as hydrochloric acid, add sufficient water to make the compound of Formula I insoluble in the medium, and collect the precipitate that forms by filtration or centrifugation. Alternately or when a solvent with limited solubility in water is used, the solvent can be at least partially removed by distillation after the acidification, water added to precipitate the product, and the product extracted with water to remove the salts and the residual solvent present.

The alkali metal alkoxide compounds of Formula IV employed in the process of the invention can be obtained in any of the conventional ways. Sodium methoxide, sodium ethoxide, and potassium t-butoxide can be purchased. These reagents can be prepared, for example, by adding sodium methoxide to the corresponding alcohol of the desired alkali metal alkoxide compound and distilling off the methanol, by adding potassium t-butoxide to said alcohol and using the t-butyl alcohol as a portion of the solvent, by adding lithium, sodium, or potassium metal to said alcohol, by adding lithium, sodium, or potassium hydride to said alcohol, or by adding an alkali metal hydroxide to said alcohol. The preparation of the alkali metal alkoxide reagent of Formula IV by the addition of solid sodium hydroxide or potassium hydroxide or of a concentrated aqueous sodium hydroxide or potassium hydroxide solution to an excess of the corresponding alcohol in a suitable solvent and then removing at least part of the water present by distillation is a preferred embodiment of the invention. An excess of the alkali metal alkoxide reagent is generally used. Amounts of the alkali metal alkoxide reagent of Formula IV of just over 1 mole when X represents chloro or bromo and just over 2 moles when X represents hydroxycarbonyl or a 1-alkyl-5-hydroxypyrazole-4-carbonyl moiety of Formula II to about 10 moles per mole of the 3-chlorobenzene compound of Formula III are typical.

The 3-chlorobenzene compounds of Formula III wherein X represents a 1-alkyl-5-hydroxypyrazole-4-carbonyl moiety of Formula II and methods for their preparation were described, for example, in U.S. Pat. No. 4,744,815 and Japanese Patent Application 63-122673, published May 26, 1988.

3-Chlorobenzene compounds of Formula III wherein X represents hydroxycarbonyl ($CO_2H$) and their preparation were described, for example, in U.S. Pat. No. 4,898,973. These benzoic acid compounds are versatile intermediates.

The 3-chlorobenzene compounds of Formula III wherein X represents chloro or bromo have not been described in the art. The compounds wherein X represents chloro, 1,2,3-trichloro-4-alkylsulfonylbenzene compounds, can be prepared by alkanesulfonation of 1,2,3-trichlorobenzene. The alkanesulfonation is generally carried out by first preparing the appropriate alkanesulfonic acid anhydride from an alkanesulfonic acid and thionyl chloride and then contacting this with 1,2,3-trichlorobenzene in the presence of trifluoromethanesulfonic acid at a temperature of about 140° C. to about 200° C. The desired product can be recovered by conventional means and the isomeric by-product obtained can be removed by recrystallization from ethanol. The compounds wherein X represents bromo, 1-bromo-2,3-dichloro-4-alkylsulfonylbenzene compounds, can be prepared by bromination and oxidation of a 2,3-dichloroalkylthiobenzene compound. The bromination is generally carried out with agitation at ambient temperature in a solvent, such as glacial acetic acid. Iron and iodine can be used as catalysts. The oxidation is generally carried out with hydrogen peroxide in a solvent, such as glacial acetic acid. The reagents are combined and heated with agitation to about 50° C. to about 90° C. The desired products can be recovered by conventional means. Other methods of preparation of these compounds using processes parallel to processes known in the art for related compounds can also be employed.

The alcohols corresponding to the alkali metal alkoxide compounds of Formula IV are well-known in the art.

2-Chloro-3-alkoxy-4-alkylsulfonylbenzoic acid compounds of Formula 1B (wherein X represents hydroxycarbonyl) including 2-chloro-3-(2-methoxyethoxy)-4-alkylsulfonylbenzoic acids, and their use in the preparation of 2-(2-chloro-3-alkoxy-4-alkylsulfonylbenzoyl)-1,3-cyclohexanedione herbicides were disclosed in U.S. Pat. No. 4,898,973.

Benzoic acid compounds of Formula IB wherein X represents hydroxycarbonyl can be converted to compounds of Formula IA by methods described in the art for some of these compounds and for related compounds. For example, the benzoic acid compound can be converted to its acid chloride with thionyl chloride, the benzoic acid chloride compound obtained condensed with a 1-alkyl-5-hydroxypyrazole compound in the presence of triethylamine, and the resulting ester isomerized by adding acetone cyanohydrin. Alternately, the benzoic acid compound can be condensed with a 1-alkyl-5-hydroxypyrazole compound in the presence of dicyclohexylcarbodimide and triethylamine and the resulting ester isomerized by adding acetone cyanohydrin. Suitable procedures are described, for example, in U.S. Pat. Nos. 4,744,815, 4,885,022, and RE-34,779.

Compounds of Formulas IB and III wherein X represents bromo can be converted into the herbicidal compounds of Formula IA by methods described herein and in the art. Such compounds are known to react with 1-alkyl-5-hydroxypyrazole and carbon monoxide under pressure in the presence of a tertiary amine base such as triethylamine, potassium carbonate, dichloro(bistriphenylphosphine) palladium catalyst, and a solvent such as dioxane to obtain compounds of Formula IA and III (wherein X represents a 1-alkyl-5-hydroxypyrazole-4-carbonyl moiety of Formula II), respectively. The process is disclosed, for example, in U.S. Pat. No. RE-34,408. Alternately, the compounds of Formulas IB and III wherein X represents bromo can converted into 2-chloro-3-substituted-4-alkylsulfonylbenzoic acid compound intermediates (Formulas IB and III wherein X represents hydroxycarbonyl) by treatment with carbon monoxide in the presence of a tertiary amine base, potassium carbonate, a dichloro(bistriphenylphosphino)palladium catalyst, an organic solvent, and water. The process can be carried out in the presence of an alcohol instead of water to obtain the corresponding esters, which can readily be hydrolyzed to the desired acids. The process is essentially the same as that given above with the exception that the 1-alkyl-5-hydroxypyrazole compound is omitted and water or an alcohol is added.

Carbonylation processes are known to work well with bromo and iodo benzene compounds, but generally not with chlorobenzene compounds. It has now been found that compounds of Formulas IB and III wherein X represents chloro, which chloro compounds can be represented by Formula V:

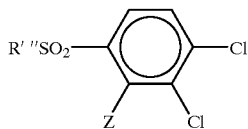

wherein

Z represents Cl or OR and R represents a $C_1$–$C_4$ alkyl group optionally substituted with a $C_1$–$C_4$ alkoxy or $C_1$–$C_4$ alkylthio group or with a 3–6 membered alicyclic moiety composed of one oxygen or sulfur atom and 2–5 carbon atoms or represents a 3–6 membered alicyclic moiety composed of one oxygen or sulfur atom and 2–5 carbon atoms; and R''' represents $C_1$–$C_4$ alkyl can be converted to compounds of Formulas IA and III wherein X represents a pyrazolecarbonyl moiety of Formula II, which compounds can be represented by Formula VI:

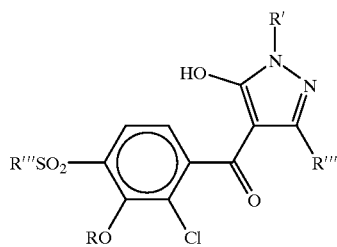

wherein
R''' and Z are as defined for compounds of Formula V;
R' represents $C_1$–$C_4$ alkyl; and
R'' represents H or $C_1$–$C_4$ alkyl
by a process which comprises contacting the chloro compound with a 1-alkyl-5-hydroxypyrazole compound of Formula VII:

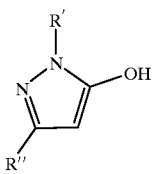

and carbon monoxide under 3,000 to 50,000 kiloPascals pressure under anhydrous conditions at a temperature of about 100° C. to about 120° C. in the presence of a non-protic solvent, a base, a catalytic amount of a catalyst comprising a palladium II halide or $C_1$–$C_8$ alkanoate and a bis(diphenylphosphino)alkane chelant selected from 1,3-bis (diphenylphosphino)propane and 1,4-bis (diphenylphosphino)butane or a preformed palladium II halide or $C_1$–$C_8$ alkanoate salt:bis(diphenylphosphino) alkane complex prepared therefrom, and, optionally, an oxygen scavenger, and, optionally, a phase transfer catalyst, and subsequently acidifying the reaction mixture obtained.

The process is preferably applied to the preparation of compounds wherein Z represents chloro or 2-methoxyethoxy, R' represents methyl or ethyl, R" represents hydrogen, and R''' represents methyl.

The stoichiometry of the process calls for one mole of carbon monoxide and one mole of 1-alkyl-5-hydroxypyrazole compound per mole of chloro compound. It is generally advantageous, however, to use an excess of both carbon monoxide and 1-alkyl-5-hydroxypyrazole compound in order to increase the rate of reaction. Up to about three moles of 1-alkyl-5-hydroxypyrazole compound per mole of chloro compound are generally employed and about 1.1 to about 2 moles are often optimum when costs are considered. The excess 1-alkyl-5-hydroxypyrazole compound can be converted to product by simply filtering the reaction mixture obtained in the process, adding more chloro compound, and repressurizing with carbon monoxide.

The process is carried out in an autoclave or pressure vessel since the process requires at least some pressure, which pressure is supplied primarily by the carbon monoxide reagent. Carbon monoxide pressures of about 3,000 to about 50,000 kiloPascals are suitable and of about 5,000 to about 15,000 kiloPascals are typically preferred. The temperature required for the process is critical and is within a very narrow range; the reaction being too slow below about 100° C. and poorly selective above about 120° C.

Suitable solvents include dioxane, tetrahydrofuran, 1,2-dimethoxyethane, and acetonitrile. It is generally advantageous to use sufficient solvent to keep the initial concentration of chloro compound below about 10 percent. Suitable bases include trialkylamines such as triethylamine and tributylamine, sodium or potassium acetate, sodium or potassium carbonate, and potassium t-butoxide. Sodium or potassium acetate, sodium or potassium carbonate, and triethylamine are often preferred. Typically about 2 to about 3 moles of base per mole of chloro compound are used.

The palladium II salt used, either separately or as a complex with a trihydrocarbylphosphine chelant, may be any halide or $C_1$–$C_8$ alkanoate. The chloride or acetate are generally preferred. The palladium II salt is generally employed in amounts of about 2 to about 10 mole percent of the chloro compound present. The trihydrocarbylphosphine chelant, either 1,3-bis(diphenylphosphino)propane or 1,4-bis(diphenylphosphino)butane, is typically used in amounts equimolar with up to about two times the molar amount of palladium II salt used. Other methods of obtaining the palladium catalysts required for the process are known in the art and can be used as equivalent alternatives to the preparative method described herein.

It is important to exclude oxygen from the reaction and this is generally readily accomplished by purging and pressurizing the reaction vessel with carbon monoxide. Any last traces of oxygen can be dealt with by adding an oxygen scavenger compound, that is, a compound that reacts readily with oxygen, such as hydroquinone, to the reaction mixture. Amounts of oxygen scavenger of up to about two percent are typically employed. Phase transfer catalysts generally accelerate the reaction and are often advantageously employed. Suitable phase transfer catalysts include crown ethers, for example, 18-crown-6, 12-crown-4, and benzo-15-crown-5; tetraalkylammonium salts, such as tetrabutylammonium bromide, methyltrioctylammonium chloride, and benzyltriethylammonium chloride; and tetraarylphosphonium salts, such as tetraphenylphosphonium bromide. Tetrabutylammonium bromide is sometimes preferred. About 3 to about 15 mole percent of the catalyst (based on chloro compound) is typically used.

The hydroxy substituent on the pyrazole ring of the product compounds of Formula VI is acidic and is in its salt form at the conclusion of the main reaction of the process. The desired acid form can be obtained by acidifying the reaction mixture produced in the main reaction in any standard way, such as by adding a mineral acid, for example, hydrochloric or sulfuric acid. Sufficient acid is generally added to convert all of the salt of the compound of Formula VI obtained to its acid form.

It has further been found that chloro compounds of Formula V:

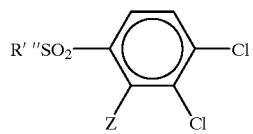

wherein
  Z represents Cl or OR and R represents a $C_1$–$C_4$ alkyl group optionally substituted with a $C_1$–$C_4$ alkoxy or $C_1$–$C_4$ alkylthio group or with a 3–6 membered alicyclic moiety composed of one oxygen or sulfur atom and 2–5 carbon atoms or represents a 3–6 membered alicyclic moiety composed of one oxygen or sulfur atom and 2–5 carbon atoms; and
  R''' represents $C_1$–$C_4$ alkyl can be converted to compounds of Formulas IB and III wherein X represents hydroxycarbonyl or alkoxycarbonyl, which compounds can be represented by Formula VIII:

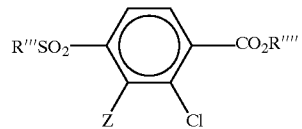

wherein
  R'''' represents H or lower alkyl; and
  R''' and Z are as defined for compounds of Formula V by a process which comprises contacting the chloro compound with carbon monoxide under 3,000 to 50,000 kiloPascals pressure at a temperature of about 100° C. to about 150° C. in the presence of water or a lower alkyl alcohol, a base, a catalytic amount of a palladium II halide or $C_1$–$C_8$ alkanoate, a trihydrocarbylphosphine chelant selected from a triphenylphosphine, a diphenylcyclohexylphosphine, 1,3-bis(diphenylphosphino)propane, and 1,4-bis(diphenylphosphino)butane or a preformed palladium II halide or $C_1$–$C_8$ alkanoate salt:trihydrocarbylphosphine complex prepared therefrom, and, optionally, a phase transfer catalyst and, when R'''' represents hydrogen, subsequently acidifying the reaction mixture obtained.

The process is often preferably applied to the preparation of compounds wherein Z represents chloro or 2-methoxyethoxy, R''' represents methyl, and R'''' represents hydrogen.

The stoichiometry of the process calls for one mole of carbon monoxide per mole of chloro compound. It is generally advantageous, however, to use an excess of carbon monoxide in order to increase the rate of reaction.

The process is carried out in an autoclave or pressure vessel since the process requires at least some pressure, which pressure is primarily supplied by the carbon monoxide reagent. Carbon monoxide pressures of about 3,000 to about 50,000 kiloPascals are suitable and of about 5,000 to about 15,000 kiloPascals are typically preferred. The temperature at which the process is conducted is important; the reaction being too slow below about 100° C. and poorly selective above about 150° C.

Suitable solvents include dioxane, tetrahydrofuran, 1,2-dimethoxyethane, acetonitrile, and t-butyl alcohol. These solvents are typically used in conjunction with water when the desired product is a compound of Formula VIII wherein R''' represents hydrogen. It is generally preferred to use the lower alcohol involved in the process (R''''OH) as a solvent, either alone or in combination with one of the above named solvents, when a compound of Formula VIII wherein R'''' represents a lower alkyl group is desired. In the foregoing lower alkyl is a 1 to 6 carbon alkyl group. Suitable bases are generally poorly nucleophilic bases and include trialkylamines such as triethylamine and tributylamine, sodium or potassium acetate, and sodium or potassium carbonate. Typically about 2 to about 3 moles of base per mole of chloro compound are used.

The palladium II salt added, either separately or as a complex with a trihydrocarbylphosphine chelant, may be any halide or $C_1$–$C_8$ alkanoate. The chloride or acetate are generally preferred. The palladium II salt is generally employed in amounts of about 2 to about 10 mole percent of the chloro compound present. When 1,3-bis (diphenylphosphino)propane or 1,4-bis(diphenylphosphino) butane are used as the trihydrocarbylphosphine chelant, the chelant is used in amounts equimolar with up to about two times the molar amount of palladium II salt. When a trihydrocarbylphosphine chelant with only one phosphorus atom is used, twice as much is required. Other methods of obtaining the palladium catalysts required for the process are known in the art and can be used as equivalent alternatives to the preparative method described herein.

Oxygen is generally excluded from the reactor and is removed by purging and pressurizing the reaction vessel with carbon monoxide. Phase transfer catalysts generally accelerate the reaction and are sometimes advantageously employed. Suitable phase transfer catalysts include crown ethers, for example, 18-crown-6, 12-crown-4, and benzo-15-crown-5; tetraalkylammonium salts, such as tetrabutylammonium bromide, methyltrioctylammonium chloride, and benzyltriethylammonium chloride; and tetraarylphosphonium salts, such as tetraphenylphosphonium bromide. Tetrabutylammonium bromide is sometimes preferred. About 3 to about 15 mole percent of the catalyst (based on chloro compound) is typically used.

The reaction mixture obtained can be neutralized in any standard way, such as by adding a mineral acid, for example, hydrochloric or sulfuric acid. Sufficient acid is typically added to convert all of the salt of the substituted benzoic acid of Formula VIII produced to the desired substituted benzoic acid.

The following examples, which are presented to illustrate the invention, should not be construed as limitations on the claims.

EXAMPLES

1. Preparation of 1-Bromo-2,3-dichloro-4-methylsulfonylbenzene

A 10 g (grams), 52 mmol (millimoles)) sample of 2,3-dichloromethylthiobenzene obtained by methylation of 2,3-dichlorobenzenethiol was dissolved in 100 mL (milliliters) of glacial acetic acid and 16.4 g (103 mmol) of bromine was added dropwise with stirring over a 20-min period. The resulting mixture was allowed to stir for another 4 hours after which most of the excess bromine was removed by distillation under reduced pressure and the remainder was removed by adding sodium meta-bisulfite until no orange color remained. Water was then added and the precipitate that formed was recovered by filtration, washed with water, and dried. The resulting 13.3 g (95 percent of theory) of a low melting solid was 1-bromo-2,3-dichloro-4-methylthiobenzene. The structure was confirmed by its $^1$H NMR spectrum (CDCl$_3$): 7.50(d, 1H, J=8.7 Hz), 6.90(d, 1H, 8.7 Hz), 2.48s, 3H).

The 13.3 g (48.9 mmol) of 1-bromo-2,3-dichloro-4-methylthiobenzene obtained was placed in 50 mL of glacial acetic acid and 13.9 g (120 mmol) of 30 percent hydrogen peroxide was added with stirring. The resulting solution was heated at 80° C. for 3 hours. Water was then added and the precipitate that formed was recovered by filtration, washed with water, and dried to obtain 14.0 g (94 percent of theory) of the title compound. A portion of this was recrystallized from ethanol to obtain a white solid melting at 173.5–175° C. Its structure was confirmed by its $^1$H NMR spectrum (CDCl$_3$): 7.95(d, 1H, J=8.4 Hz), 7.79(d, 1H, 8.4 Hz), 3.29(s, 3H) and its $^{13}$C NMR spectrum (CDCl$_3$): 139.2, 136.5, 132.4, 132.2, 130.4, 129.0, 42.7.

2. Preparation of 1,2,3-Trichloro-4-methylsulfonylbenzene

A mixture of 133 g (1.38 mol) of methanesulfonic acid and 67 g (0.56 mol) of thionyl chloride was heated to reflux with stirring for one hour. The temperature increased from 50° C. to 160° C. as the reaction to form methanesulfonic acid anhydride progressed. The resulting mixture was cooled to below 50° C. and then 50.0 g (0.28 mol) of 1,2,3-trichlorobenzene and 4.2 g (0.028 mol) of trifluoromethanesulfonic acid were added. This mixture was heated with stirring and allowed to react at 140° C. for 18 hours and at 160° C. for 2 hours. The resulting mixture solidified on cooling. It was taken up in 600 mL of dichloromethane and the resulting solution was washed with 2×100 mL of water, 100 mL of 1 M aqueous sodium bicarbonate solution, and 100 mL of water, dried over sodium sulfate, and concentrated by evaporation under reduced pressure to obtain 58.5 g of a 9:1 mixture of the title compound and its isomer. This was recrystallized from ethanol to obtain 46 g (63 percent of theory) of the title compound as a white solid melting at 159–160° C. The structure was confirmed by its $^1$H NMR spectrum (CDCl$_3$): 8.02(d, 1H, J=8.6 Hz), 7.60(d, 1H, 8.7 Hz), 3.28(s, 3H) and its $^{13}$C NMR spectrum (CDCl$_3$): 140.1, 138.5, 134.6, 132.8, 126.7, 42.6.

3. Preparation of 1-Ethyl-4-(2,3-dichloro-4-methylsulfonylbenzoyl)-5-hydroxypyrazole Thionyl chloride (3.5 g, 6.7 mmol) was added to a slurry of 1.3 g (4.8 mmol) of 2,3-dichloro-4-methylsulfonylbenzoic acid in 10 mL of toluene with stirring and the mixture was heated at reflux until a homogeneous solution was obtained, which required about 45 min. The volatile components of the mixture were removed by evaporation under reduced pressure and the residual acid chloride was taken up in 10 mL of dichloromethane. This solution was combined with a solution of 5.4 g (4.8 mmol) of 1-ethyl-5-hydroxypyrazole dissolved in 6.2 mL of 1 N aqueous sodium hydroxide solution diluted with 5 mL of water with stirring at ambient temperature. After 1 hour, the pH was adjusted to 8 by adding 1 M aqueous sodium bicarbonate. The phases present were separated and the aqueous phase was extracted with 3 mL of dichloromethane. The organic phase and extract were combined, washed with 5 mL of water, dried over sodium sulfate, filtered, and concentrated by evaporation under reduced pressure. The residue was taken up in 15 mL of anhydrous dioxane and 730 mg (5.3 mmol) of solid potassium carbonate was added. The mixture was heated at 90° C. with stirring for 2 hours and then another 100 mg of potassium carbonate and 2–3 drops of acetone cyanohydrin were added. Heating and stirring were continued for another 30 min and then the mixture was cooled and poured into 15 mL of water. The phases were separated and the aqueous phase was extracted with 2×5 mL of dichloromethane. The aqueous phase was then acidified with 6 N aqueous hydrochloric acid and the solids that formed were extracted with 2×5 mL of dichloromethane. All of the organic phases and extracts were combined, washed with 5 mL of water, dried over sodium sulfate, filtered, and concentrated by evaporation under reduced pressure. The residue, which amounted to 1.4 g (80 percent of theory), was recrystallized from aqueous ethanol to obtain the title compound as a white solid melting at 198–200° C.

4. Preparation of 1-Bromo-2-chloro-3-(2-methoxyethoxy)-4-methylsulfonylbenzene from 1-Bromo-2,3-dichloro-4-methylsulfonylbenzene A) Sodium hydride (87 mg (milligrams), 3.6 mmol) was slurried in 5 mL of anhydrous tetrahydrofuran and 325 mg (4.3 mmol) of 2-methoxyethanol was added with stirring. When the hydrogen evolution ceased, 1.1 g (3.3 mmol) of 1-bromo-2,3-dichloro-4-methylsulfonylbenzene was added with stirring and allowed to react at 25° C. for 2 hours. Dichloromethane was added and the resulting mixture was extracted with water, dried over sodium sulfate, and concentrated under reduced pressure to obtain 1.0 g (88 percent of theory) of the title compound as a low melting solid. The product was identified to be the title compound by its $^1$H NMR spectrum (CDCl$_3$): 7.77(d, 1H, J=8.4 Hz), 7.61(d, 1H, 8.4 Hz), 4.41(t, 2H, J=4.2 Hz), 3.65(t, 2H, J=4.2 Hz), 3.52(s, 3H), 3.29(s, 3H) and its $^{13}$C NMR spectrum (CDCl$_3$): 154.4, 140.3, 134.8, 129.3, 127.4, 126.1, 58.9, 43.6. The product also contained small amounts of the by-products 1-(2-methoxyethoxy)-2,3-dichloro-4-methylsulfonylbenzene and 1,3-di(2-methoxyethoxy)-2-chloro-4-methylsulfonylbenzene. A small sample was purified by recrystallization from 50 percent methanol/water to obtain white needles melting at 76.5–77.5° C.

B) Sodium metal (1.51 g, 66 mmol) was added to a solution of 5.0 g (66 mmol) of 2-methoxyethanol in 175 g of 1,1-dimethylethanol with stirring and when the hydrogen evolution ceased, the mixture was heated to 50° C. and 19.9 g (66 mmol) of 1-bromo-2,3-dichloro-4-methylsulfonylbenzene was added with stirring. After 16 hours, the mixture containing the title compound was used for further synthesis.

5. Preparation of 1,2-Dichloro-3-(2-methoxyethoxy)-4-methylsulfonylbenzene from 1,2,3-Trichloro-4-methylsulfonylbenzene A) Sodium hydride (26 mg, 1.1 mmol) was slurried in 4 mL of anhydrous tetrahydrofuran and 99 mg (1.3 mmol) of 2-methoxyethanol was added with stirring. When the hydrogen evolution ceased, 250 mg (1.0 mmol) of 1,2,3-trichloro-4-methylsulfonylbenzene was added with stirring and allowed to react at 25° C. for 3.5 hours. Dichloromethane was added and the resulting mixture was extracted with water, dried over sodium sulfate, and concentrated under reduced pressure to obtain 300 mg (100 percent of theory) of the title compound as a low melting solid. The product was identified to be the title compound by its $^1$H NMR spectrum (CDCl$_3$): 7.83(d, 1H, J=8.4 Hz), 7.43(d, 1H, 8.4 Hz), 4.40(t, 2H, J=4.5 Hz), 3.84(t, 2H, J=4.2 Hz), 3.47(s, 3H), 3.28(s, 3H) and its $^{13}$C NMR spectrum (CDCl$_3$): 154.4, 140.3, 134.8, 129.3, 127.4, 126.1, 58.9, 43.6.

B) A solution of sodium 2-methoxyethoxide in 2-methoxyethanol was prepared by slowly adding 246 g (3.2 mol) of 2-methoxyethanol to 14.7 g (0.64 mol) of sodium metal and then heating the mixture to 60° C. with stirring until all the sodium dissolved. The amber solution obtained was added with stirring over a 2-hour period to a slurry of 150 g (0.58 mol) of 1,2,3-trichloro-4-methylsulfonylbenzene in 500 mL of dioxane. The mixture was then heated at 40° C. with stirring for 3 hours. The resulting mixture was cooled and 200 mL of water was added. Most of the dioxane was removed by distillation under reduced pressure and then 50 mL of ethanol was added. The two phase system was heated to reflux to coalesce the phases and then 25 mL of hexane was added. The mixture was allowed to cool with stirring overnight during which time the title compound precipitated. The precipitate was collected by filtration, washed with water, and dried to obtain 17 g (85 percent of theory) of 98 percent purity title compound as a powdery, cream colored solid. A small sample was purified by recrystallization from 50 percent methanol/water to obtain white needles melting at 69–69.5° C.

6. Preparation of 2,3-Dichloro-4-methylsulfonylbenzoic Acid from 1,2,3-Trichloro-4-methylsulfonylbenzene A) A mixture of 260 mg (1.0 mmol) of 1,2,3-trichloro-4-methylsulfonylbenzene, 168 mg (2.0 mmol) of sodium acetate, 10 mL of t-butanol, and 1 mL of water was prepared in a pressure reactor and deaerated by purging with nitrogen. To this was added 11 mg (0.05 mmol) of palladium acetate and 54 mg (0.20 mmol) of 1,4-bis(diphenylphosphino)butane and the resulting mixture was frozen by means of an dry ice/acetone bath. A pea sized piece of dry ice was added, the reactor was sealed, and pressured to 100 psi (6900 kiloPascals) with carbon monoxide, and the mixture was allowed to warm to ambient. The pressure rose to about 300 psi (about 20,700 kiloPascals). The mixture was heated to 125° C. with stirring and held for 20 hours. The reactor was then allowed to cool and the pressure was released. The pH of the mixture was adjusted to 10 by adding aqueous sodium hydroxide and the volatiles were removed by evaporation under reduced pressure. The residue was taken up in 7 mL of water and the resulting solution was extracted with 2×5 mL of dichloromethane and acidified with aqueous hydrochloric acid. The resulting mixture was extracted with ether and the ether extract was washed with 5 mL of water, dried over sodium sulfate, and concentrated by evaporation under reduced pressure to obtain 250 mg (93 percent of theory) of the title compound.

B) A mixture of 260 mg (1.0 mmol) of 1,2,3-trichloro-4-methylsulfonylbenzene, 86 mg (1.05 mmol) of sodium acetate, and 10 mL of anhydrous ethanol was prepared in a 45 mL pressure reactor and deaerated by purging with nitrogen. To this was added 11 mg (0.05 mmol) of palladium acetate and 33 mg (0.08 mmol) of 1,3-bis(diphenyphosphino)propane and the reactor was sealed taking care to exclude oxygen. The reactor was then pressured to 60 psi (4100 kiloPascals) with carbon monoxide and heated at 150° C. with stirring for 54 hours. The reactor was then allowed to cool and the pressure was released. The mixture, which contained the ethyl ester of the title compound, was basified by adding 0.5 mL of 5 N aqueous sodium hydroxide and allowed to stir for 1 hour. The volatiles were then removed by evaporation under reduced pressure and the residue was taken up in 5 mL of water. The resulting solution was extracted with 2×5 mL of dichloromethane and acidified with 6 N aqueous hydrochloric acid. The resulting mixture was extracted with 10 mL of ether and the ether extract was washed with 5 mL of water, dried over sodium sulfate, and concentrated by evaporation under reduced pressure to obtain 190 mg (70 percent of theory) of the title compound.

7. Preparation of 2-Chloro-3-(2-methoxyethoxy)-4-methylsulfonylbenzoic Acid from 1,2-Dichloro-3-(2-methoxyethoxy)-4-methylsulfonylbenzene A mixture of the following was placed in a pressure vessel: 130 g (0.43 mol) of 1,2-dichloro-3-(2-methoxyethoxy)-4-methylsulfonylbenzene, 250 g of water, 250 g of t-butyl alcohol, 101.2 g (0.95 mol) of sodium carbonate, 1.15 g (4.3 mmol) of palladium acetate, and 3.7 g (8.6 mmol) of 1,4-bis(diphenylphosphino)butane. The vessel was sealed, purged with carbon monoxide, pressured to 150 psi (10,300 kiloPascals) with carbon monoxide, and heated to 125° C. with stirring for 16 hours. The mixture was allowed to partially cool and was then added to a warm mixture of toluene and water. The aqueous phase was recovered, washed with toluene, and acidified with 6 N aqueous hydrochloric acid at 60° C. The oil that formed was extracted into dichloromethane and the extract was concentrated by evaporation under reduced pressure. The residue was dissolved in dilute aqueous sodium hydroxide and the solution obtained was added slowly to an 80:20 mixture of 6 N aqueous hydrochloric acid and ethanol. The precipitate that formed was recovered by filtration and recrystallized from a mixture of ethanol and water to obtain 66.5 g (22 percent of theory) of the title compound as a dark tan solid. A further purified material was a white solid.

8. Preparation of 2-Chloro-3-(2-methoxyethoxy)-4-methylsulfonylbenzoic Acid from 2,3-Dichloro-4-methylsulfonylbenzoic Acid A solution of potassium 2-methoxyethoxide in 2-methoxyethanol was prepared by adding 17.5 g (156 mmol) of potassium t-butoxide to 103 mL of 2-methoxyethanol under nitrogen with stirring. To this was added 14.0 g (52 mmol) of 2,3-dichloro-4-methylsulfonylbenzoic acid and the resulting mixture was heated at reflux (124° C.) for between 4 and 5 hours. Most of the volatile components of the mixture were removed by concentration under reduced pressure and the residue was diluted with water. The resulting mixture was extracted twice with ether and then acidified by adding 1 N aqueous hydrochloric acid. The acidified mixture was twice extracted with dichloromethane and the combined organic extracts were washed with water, dried over magnesium sulfate, filtered, and concentrated by evaporation under reduced pressure. The resulting dark brown oil was crystallized from a mixture of ethanol, ether, and petroleum ether by trituration with the aid of a seed crystal to obtain 12.7 g (79 percent of theory) of the title compound.

9. Preparation of 1-Ethyl-4-(2-chloro-3-(2-methoxyethoxy)-4-methylsulfonylbenzoyl)-5-hydroxypyrazole from 1-Bromo-2-chloro-3-(2-methoxyethoxy)-4-methylsulfonylbenzene A mixture of 345 mg (1.0 mmol) of 1-bromo-2-chloro-3-(2-methoxyethoxy)-4-methylsulfonylbenzene, 250 mg (2.2 mmol) of 1-ethyl-5-hydroxypyrazole, 840 mg (8.0 mmol) of triethylamine, 21 mg (0.030 mmol) of palladium (bistriphenylphosphine)dichloride, and 10 mL of anhydrous, deaerated acetonitrile was placed in a 45 mL pressure reactor containing a magnetic stirring bar. The reactor was sealed, purged with carbon monoxide, and pressurized to 130 psi (pounds per square inch) (9,000 kiloPascals) pressure with carbon monoxide. The mixture was heated at 100° C. with stirring for 14 hours and then another 35 mg of catalyst was added and the reactor was repressurized with carbon monoxide and allowed to react another 24 hours at 100° C. After cooling the reactor and releasing the pressure, the mixture was concentrated by evaporation under reduced pressure. The residue was diluted with 10 mL of water and with 10 mL of dichloromethane and was basified with aqueous sodium hydroxide. The aqueous phase was recovered, washed with 2×5 mL of dichloromethane, and acidified to pH 0.5 with 6 N aqueous hydrochloric acid. The mixture was then extracted with dichloromethane and the solution obtained was washed with water, dried over sodium sulfate, and concentrated by evaporation under reduced pressure to obtain 100 mg (25 percent of theory) of the title compound.

10. Preparation of 1-Ethyl-4-(2-chloro-3-(2-methoxyethoxy)-4-methylsulfonylbenzoyl)-5-hydroxypyrazole from 1,2-Dichloro-3-(2-methoxyethoxy)-4-methylsulfonylbenzene A solution of 10.0 g (35 mmol) of 1,2-dichloro-3-(2-methoxyethoxy)-4-methylsulfonylbenzene in 500 g of anhydrous dioxane was placed in a 1 L Hastalloy C pressure reactor equipped with a mechanical stirrer and was purged with nitrogen. The following were then added: 7.48 g (70 mmol) of 1-ethyl-5-hydroxypyrazole, 8.16 g (77 mmol of sodium carbonate, 0.195 g (1.75 mmol) of palladium acetate, 0.37 g (1.75 mmol) of 1,4-bisdiphenylphosphinobutane, 0.19 g (0.35 mmol) of hydroquinone, and 0.56 g (3.5 mmol) of tetrabutylammonium bromide. The reactor was sealed and purged three times with carbon monoxide, pressuring to about 200 psi (about 13,800 kiloPascals) each time and was then pressured to 150 psi (10,300 kiloPascals). The mixture was heated to 100–105° C. with stirring, the pressure was adjusted to 175–200 psi (12,000 to 13,800 kiloPascals), and the reaction was allowed to proceed for about 50 hours. About 500 mL of water was added and the bulk of the dioxane was removed by evaporation under reduced pressure. The resulting mixture was filtered to remove spent catalyst, washed twice with 30 mL portions of toluene, and poured slowly with stirring into 200 mL of 10 percent aqueous hydrochloric acid, keeping the temperature at about 60° C. The yellow solution obtained was allowed to cool and the precipitate that formed was collected by filtration, washed with water, and dried to obtain 9.0 g (59 percent of theory) of the title compound.

11. Preparation of 1-Ethyl-4-(2-chloro-3-(2-methoxyethoxy)-4-methylsulfonylbenzoyl)-5-hydroxypyrazole from 1-Ethyl-4-(2,3-dichloro-4-methylsulfonylbenzoyl)-5-hydroxypyrazole A) A mixture of 38.7 g (0.10 mol) of 93.8 percent 1-ethyl-4-(2,3-dichloro-4-methylsulfonylbenzoyl)-5-hydroxypyrazole, 198.9 g (2.62 mol) of 2-methoxyethanol, and 12.2 g (0.30 mol) of 98.3 percent sodium hydroxide pellets was stirred until the sodium hydroxide pellets dissolved and was then distilled under reduced pressure at 25–30° C. to remove 76.5 g of a mixture of water and 2-methoxyethanol. The mixture then contained 1.16 percent water (uncorrected for hydroxide) as determined by Karl Fischer titration. The mixture was then heated with stirring at 80° C. for 3.8 hours. Another 24.9 g of 2-methoxyethanol was removed by distillation under reduced pressure. The mixture was then allowed to cool to near ambient temperature and 195.9 g of water was added. The resulting mixture was heated to 60° C., acidified to pH 1 by slowly adding 65.5 g of 6.25 N aqueous hydrochloric acid with stirring, and allowed to react for 30 min. The mixture was allowed to cool slowly with stirring overnight and the light yellow precipitate that formed was recovered by filtration and washed with 50 g of cold water and then 40.2 g of ethanol. It was then dried under reduced pressure at 53° C. overnight to obtain 36.2 g (84.4 percent of theory) of the title compound as a 93.4 percent purity, pale yellow solid.

B) Sodium hydride (30 mg, 1.2 mmol) was cautiously added to 5 mL of anhydrous 2-methoxyethanol with stirring under a nitrogen atmosphere. When the evolution of hydrogen ceased the mixture was a homogeneous solution. 1-Ethyl-4-(2,3-dichloro-4-methylsulfonylbenzoyl)-5-hydroxypyrazole (150 mg, 0.41 mmol) was added and the mixture heated to 70° C. with stirring and held for 18 hours. The mixture obtained was allowed to cool and then 10 mL of water and 6 N aqueous hydrochloric acid were added. The acidified mixture was extracted with 2×5 mL of dichloromethane and the extract was washed with 5 mL of water, dried over sodium sulfate, filtered, and concentrated by evaporation under reduced pressure. The oily residue was further heated at 80° C. under 0.5 mm Hg (0.067 kiloPascals) pressure to remove volatiles and obtain 140 mg (85 percent of theory) of oil. This oil was crystallized from aqueous ethanol to obtain the title compound as a white solid melting at 158–159° C.

C) A mixture of 50.0 g (0.122 moles) of 1-ethyl-4-(2,3-dichloro-4-methylsulfonylbenzoyl)-5-hydroxypyrazole of 88.9% purity, 250 g of 2-methoxyethanol, and 33.1 g (0.413 moles) of 50 percent aqueous sodium hydroxide was prepared in a 500 mL flask equipped with a distillation head and was heated to 80° C. with stirring under 60 mm Hg (8 kiloPascals) pressure. Water and some 2-methoxyethanol were removed by distillation at a reflux ratio of 10/1 for 4 hours at which time the head temperature reached 55° C. at 80 mm Hg (11 kiloPascals) pressure and 64.7 g of distillate had been recovered. The mixture was heated for 4 hours at 80° C. with stirring without further distillation at which point the reaction was complete. The 268.4 g of reaction mixture obtained was analyzed by high pressure liquid phase chromatography and found to contain 46.4 g (91.3 percent of theory) of the title compound as its sodium salt. The mixture was also analyzed by Karl Fischer titration and found to contain 460 ppm (parts per million) of water. Two additional runs were made with smaller amounts of 2-methoxyethanol and the combined total amount of title compound obtained (as its sodium salt) was 143.3 g (97.3 percent of theory). A 140.5 g portion of the combined reaction mixtures containing 32.0 g of the title compound in the form of its sodium salt was warmed to 60° C. and 130 g of water was added dropwise with stirring. The mixture was then acidified to an apparent pH of 0.9 by the dropwise addition with stirring of about 19 mL of 36 percent aqueous hydrochloric acid. The acidified mixture was cooled to 5° C. and held for about 30 minutes. The precipitate that formed was recovered by filtration, washed with 100 g of water, and dried under a heat lamp overnight to obtain 31.2 g. of the title compound of 95.8 percent purity. The recovery yield was 97.4 percent and the overall yield of the title compound in the process was 94.8 percent.

What is claimed is:

1. A process for the preparation of 3-alkoxybenzene compounds of the formula:

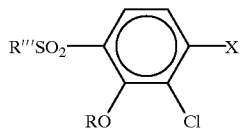

wherein

X represents Cl, Br, $CO_2H$, or a 1-alkyl-5-hydroxypyrazole-4-carbonyl moiety of the formula:

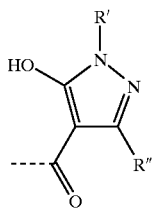

R represents a $C_1$–$C_4$ alkyl group unsubstituted or substituted with a $C_1$–$C_4$ alkoxy or $C_1$–$C_4$ alkylthio group or with a 3–6 membered alicyclic moiety having one oxygen or sulfur atom and 2–5 carbon atoms or represents a 3–6 membered alicyclic moiety having one oxygen or sulfur atom and 2–5 carbon atoms;

R" represents H or $C_1$–$C_4$ alkyl; and

R' and R'" each independently represents $C_1$—$C_4$ alkyl;

which process comprises causing a 3-chlorobenzene compound of the formula:

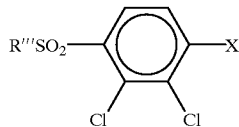

wherein X and R'" are as defined hereinabove to react with an alkali metal alkoxide compound of the formula:

$$RO^- \, M$$

wherein

R is as defined hereinabove and $M^+$ represents lithium, sodium, or potassium cation in a liquid medium, optionally in the presence of a phase transfer catalyst, at a temperature of about 20° C. to about 110° C.

2. A process according to claim 1 wherein R represents $C_1$–$C_4$ alkyl or 2-($C_1$–$C_4$ alkoxy)ethyl.

3. A process according to claim 1 wherein X represents a 1-alkyl-5-hydroxypyrazole-4-carbonyl moiety of the formula:

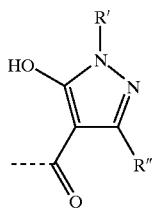

wherein

R" represents H or $C_1$–$C_4$ alkyl; and

R' represents $C_1$–$C_4$ alkyl.

4. A process according to claim 3 wherein R' represents methyl or ethyl and R" represents hydrogen.

5. A process according to claim 1 wherein R'" represents methyl.

6. A process according to claim 1 wherein $M^+$ represents sodium or potassium cation.

7. A process according to claim 1 wherein the liquid medium comprises the alcohol R—OH having the same R group as the alkali metal alkoxide compound used.

8. A process according to claim 1 wherein the process is carried out at a temperature of about 40° C. to about 90° C.

9. A process according to claim 1 wherein the medium contains less than about 500 ppm water.

10. A process according to claim 1 wherein a phase transfer catalyst is used.

11. A compound of the formula:

R'''SO₂—⟨benzene ring with X, Cl, OR substituents⟩—X
            |         |
           RO        Cl wherein X represents Cl or Br;

R represents a $C_1$–$C_4$ alkyl group unsubstituted or substituted with a $C_1$–$C_4$ alkoxy or $C_1$–$C_4$ alkylthio group or with a 3–6 membered alicyclic moiety having one oxygen or sulfur atom and 2–5 carbon atoms or represents a 3–6 membered alicyclic moiety having one oxygen or sulfur atom and 2–5 carbon atoms; and R''' represents $C_1$–$C_4$ alkyl.

12. A compound according to claim 11 wherein R represents $C_1$–$C_4$ alkyl or 2-($C_1$–$C_4$ alkoxy)ethyl.

13. A compound according to claim 11 wherein R''' represents methyl.

14. A process for preparing compounds of the formula:

⟨pyrazole-HO, R', R'', linked via C(=O) to benzene ring bearing R'''SO₂, RO, Cl, R'''⟩ wherein

Z represents Cl or OR and R represents a $C_1$–$C_4$ alkyl group unsubstituted or substituted with a $C_1$–$C_4$ alkoxy or $C_1$–$C_4$ alkylthio group or with a 3–6 membered alicyclic moiety having one oxygen or sulfur atom and 2–5 carbon atoms or represents a 3–6 membered alicyclic moiety having one oxygen or sulfur atom and 2–5 carbon atoms;

R' and R''' each individually represents $C_1$–$C_4$ alkyl; and

R'' represents H or $C_1$–$C_4$ alkyl which process comprises causing a chloro compound of the formula:

R'''SO₂—⟨benzene ring⟩—Cl with Z and Cl substituents wherein Z and R''' are as defined hereinabove to react with a 1-alkyl-5-hydroxypyrazole compound of the formula:

⟨pyrazole with R', R'', OH⟩ wherein R' and R'' are as defined hereinabove and carbon monoxide under 3,000 to 50,000 kiloPascals pressure under anhydrous conditions at a temperature of about 100° C. to about 120° C. in the presence of a non-protic solvent, a base, a catalytic amount of a catalyst comprising a palladium II halide or $C_1$–$C_8$ alkanoate and a bis(diphenylphosphino)alkane chelant selected from 1,3-bis (diphenylphosphino)propane and 1,4-bis (diphenylphosphino)butane or a preformed palladium II halide or $C_1$–$C_8$ alkanoate salt:bis(diphenylphosphino) alkane complex prepared therefrom, and in the presence or absence of an oxygen scavenger, and in the presence or absence of a phase transfer catalyst, and subsequently acidifying the reaction mixture obtained.

15. A process according to claim 14 wherein the palladium II salt is palladium chloride or palladium acetate.

16. A process according to claim 14 wherein the base is sodium or potassium acetate, sodium or potassium carbonate, or triethylamine.

17. A process according to claim 14 wherein the palladium II salt and the bis(diphenylphosphino)alkane chelant are added separately.

18. A process according to claim 14 wherein Z represents chloro and R''' represents methyl.

19. A process according to claim 14 wherein R' represents methyl or ethyl and R'' represents hydrogen.

20. A process according to claim 14 carried out in the presence of a phase transfer catalyst.

* * * * *